United States Patent [19]
Briggs et al.

[11] Patent Number: 5,976,521
[45] Date of Patent: Nov. 2, 1999

[54] ANTI-ACNE COSMETIC COMPOSITIONS

[75] Inventors: Gillian Scott Briggs, Egham; Teresa Barbara Crook, Camberley; Graeme Douglas T. Smith, Windsor, all of United Kingdom

[73] Assignee: The Procter & Gamble Company, Cincinnati, Ohio

[21] Appl. No.: 08/836,231

[22] PCT Filed: Aug. 8, 1995

[86] PCT No.: PCT/US95/10135

§ 371 Date: Feb. 28, 1997

§ 102(e) Date: Feb. 28, 1997

[87] PCT Pub. No.: WO96/04894

PCT Pub. Date: Feb. 22, 1996

[30] Foreign Application Priority Data

Aug. 9, 1994 [GB] United Kingdom .................. 9416050

[51] Int. Cl.⁶ .......................... A61K 31/00; A61K 31/20; A61K 31/74; A61K 47/12

[52] U.S. Cl. .................... 424/78.07; 424/78.02; 424/78.03; 514/558; 514/772.3; 514/844; 514/859; 514/887; 514/937; 514/941

[58] Field of Search ............... 424/78.02, 78.03, 424/78.07; 514/558, 772.3, 844, 859, 887, 937, 941

[56] References Cited

U.S. PATENT DOCUMENTS

| | | | |
|---|---|---|---|
| 3,821,370 | 6/1974 | Tenta | 424/145 |
| 4,507,319 | 3/1985 | Barratt et al. | 514/546 |
| 4,542,129 | 9/1985 | Orentreich | 514/178 |
| 4,603,146 | 7/1986 | Kligman | 514/559 |
| 4,608,370 | 8/1986 | Aronsohn | 514/159 |
| 4,612,331 | 9/1986 | Barratt et al. | 514/558 |
| 4,720,353 | 1/1988 | Bell | 252/309 |
| 4,767,750 | 8/1988 | Jacquet et al. | 514/159 |
| 4,800,197 | 1/1989 | Kowcz | 514/162 |
| 4,877,805 | 10/1989 | Kligman | 514/381 |
| 4,888,342 | 12/1989 | Kligman | 514/419 |
| 4,891,227 | 1/1990 | Thaman et al. | 424/443 |
| 4,891,228 | 1/1990 | Thaman et al. | 424/443 |
| 4,938,960 | 7/1990 | Ismail | 424/195 |
| 5,001,156 | 3/1991 | Philippe et al. | 514/555 |
| 5,017,367 | 5/1991 | Stojkoski | 424/63 |
| 5,196,187 | 3/1993 | Nicoll et al. | 424/70 |
| 5,262,407 | 11/1993 | Leveque et al. | 514/159 |
| 5,573,759 | 11/1996 | Blank | 424/60 |
| 5,595,984 | 1/1997 | Blank | 514/159 |
| 5,597,813 | 1/1997 | Blank | 514/159 |
| 5,597,814 | 1/1997 | Blank | 514/159 |
| 5,604,212 | 2/1997 | Blank | 514/159 |
| 5,605,894 | 2/1997 | Blank et al. | 514/159 |
| 5,616,572 | 4/1997 | Blank | 514/159 |
| 5,620,965 | 4/1997 | Blank | 514/159 |
| 5,629,301 | 5/1997 | Blank | 514/159 |
| 5,652,229 | 7/1997 | Blank | 514/159 |
| 5,652,230 | 7/1997 | Blank | 514/159 |
| 5,691,327 | 11/1997 | Blank | 514/159 |

FOREIGN PATENT DOCUMENTS 849433  9/1960  United Kingdom .

OTHER PUBLICATIONS

Todd, et al., "Volatile Silicone Fluids for Cosmetic Formulations", *Cosmetics and Toiletries*, vol. 91, pp. 29–32, 1976.

*Primary Examiner*—Jose' G. Dees
*Assistant Examiner*—Michael A. Williamson
*Attorney, Agent, or Firm*—Loretta J. Henderson; George W. Allen; David L. Suter

[57] ABSTRACT

An anti-acne cosmetic composition in the form of a multiple phase water-in-oil emulsion and process for preparing thereof, wherein the composition comprises two or more aqueous phases and a coalescence inhibitor for preventing coalescence of the aqueous phases and wherein at least a first aqueous phase comprises the anti-acne active in the form of an aqueous/alcoholic solution. The composition exhibits moisturisation, anti-acne activity and skin anti-ageing benefits, together with product and colour stability.

30 Claims, No Drawings

ANTI-ACNE COSMETIC COMPOSITIONS

This application is a 371 of PCT/US95/10135 filed Aug. 8, 1995.

TECHNICAL FIELD

The present invention relates to cosmetic compositions. In particular it relates to tinted cosmetic compositions which provide excellent moisturisation, together with improved anti-acne activity and skin anti-ageing benefits and formulation and colour stability.

BACKGROUND OF THE INVENTION

Skin is made up of several layers of cells which coat and protect the keratin and collagen fibrous proteins that form the skeleton of its structure. The outermost of these layers, referred to as the stratum corneum, is known to be composed of 250 Å protein bundles surrounded by 80 Å thick layers. Anionic surfactants and organic solvents typically penetrate the stratum corneum membrane and, by delipidization (i.e. removal of the lipids from the stratum corneum), destroy its integrity. This destruction of the skin surface topography leads to a rough feel and may eventually permit the surfactant or solvent to interact with the keratin, creating irritation.

It is now recognised that maintaining the proper water gradient across the statum corneum is important to its functionality. Most of this water, which is sometimes considered to be the stratum corneum's plasticizer, comes from inside the body. If the humidity is too low, such as in a cold climate, insufficient water remains in the outer layers of the stratum corneum to properly plasticize the tissue; and the skin begins to scale and becomes itchy. Skin permeability is also decreased somewhat when there is inadequate water across the stratum corneum. On the other hand, too much water on the outside of the skin causes the stratum corneum to ultimately sorb three to five times its own weight of bound water. This swells and puckers the skin and results in approximately a two to three fold increase in the permeability of the skin to water and other polar molecules.

Thus, a need exists for compositions which will assist the stratum corneum in maintaining its barrier and water retention functions at optimum performance in spite of deleterious interactions which the skin may encounter in washing, work, and recreation.

Conventional cosmetic cream and lotion compositions as described, for example, in Sagarin, Cosmetics Science and Technology, 2nd Edition, Vol. 1, Wiley Interscience (1972) and Encyclopaedia of Chemical Technology, Third Edition, Volume 7 are known to provide varying degrees of emolliency, barrier and water-retention (moisturising) benefits. However, they can also suffer serious negatives in terms of skin feel (i.e. they often feel very greasy on the skin) as well as having poor rub-in, absorption and residue characteristics.

It would also be desirable to provide a cosmetic composition which delivered pigments to the skin of the user at the same time as providing excellent moisturisation. A pigmented cosmetic composition can serve to even skin tone and texture and to hide pores, imperfections, fine lines and the like.

At the same time, it would be desirable to provide a moisturising composition having topical anti-acne activity. There are many compounds which are known to exhibit anti-acne properties when applied topically to the skin. A commonly used keratolytic agent having anti-acne activity is salicylic acid. As salicylic acid is virtually insoluble in water however, it is difficult to incorporate into the aqueous phase of an emulsion composition. Delivery of salicylic acid from the pigment-containing oil phase of an emulsion composition can, on the other hand, lead to discolouration of the composition due to interaction between the salicylic acid and pigments, especially of the iron oxide type. Furthermore, in compositions requiring high water levels, such as skin moisturising compositions, salicylic acid tends to precipitate out of solution. It would therefore be desirable to deliver salicylic acid in soluble form from the aqueous phase but without the salicylic acid precipitating out of solution.

It is accordingly one object of the present invention to provide a cosmetic composition which exhibits anti-acne activity together with moisturisation benefits.

It is a further object of the invention to provide a cosmetic composition in the form of a multiple phase emulsion having improved product and colour stability.

SUMMARY OF THE INVENTION

According to one aspect of the present invention there is provided an anti-acne cosmetic composition in the form of a multiple phase water-in-oil emulsion, wherein the composition comprises:
(a) two or more aqueous phases; and
(b) a coalescence inhibitor for preventing coalescence of the aqueous phases;
and wherein at least a first aqueous phase comprises an anti-acne active in the form of an aqueous/alcoholic solution.

According to the present invention there is also provided a process for preparing an anti-acne composition, the process comprising the steps of:
(a) preparing the first aqueous phase by dissolving the anti-acne active in an aqueous/alcoholic solution;
(b) admixing the first aqueous phase with the oil phase; and
(c) subsequently adding one or more additional aqueous phase or phases to the resulting mixture to form the multiple phase water-in-oil emulsion, the first and/or additional aqueous phase or phases having dissolved therein the coalescence inhibitor.

The compositions of the present invention provide anti-acne activity and skin anti-ageing benefits, together with improved product and colour stability and superior moisturisation, skin feel and appearance.

All levels and ratios are by weight of total composition, unless otherwise indicated.

DETAILED DESCRIPTION OF THE INVENTION

The compositions of the present invention are multiple phase water-in-oil emulsions which comprise two or more aqueous phases. At least a first aqueous phase comprises an anti-acne active in the form of an aqueous/alcoholic solution. Suitable anti-acne actives for use herein include salicylic acid, retinoic acid, azelaic acid, lactic acid, glycolic acid, pyruvic acid, flavonoids, and derivatives and salts thereof, and mixtures thereof.

The anti-acne active used in the composition herein is preferably selected from salicylic acid and azelaic acid, and mixtures thereof, more preferably salicylic acid. The anti-acne active is present at a level of from about 0.1% to about 10%, preferably from about 0.1% to about 5%, more preferably from about 0.5% to about 3%, by weight of composition.

The anti-acne active is solubilized in water or an alcoholic solution, for example, solutions based upon $C_2$–$C_6$ alcohols, diols and polyols, preferred alcohols being selected from ethanol, dipropylene glycol, butylene glycol, hexylene glycol, and mixtures thereof. Alcohol is preferably present in the compositions herein at a level of from about 1% to about 20%. The final aqueous/alcoholic anti-acne active solution preferably has a pH at ambient temperature (25° C.) of less than about $pK_a+1$, where $pK_a$ is the logarithmic acidity constant for the fully protonated anti-acne active. In preferred embodiments, the pH of the final solution is less than about $pK_a$.

The logarithmic acidity constant is thus defined by reference to the equilibrium $$H^+ + H_{n-1}A = H_nA$$

where $H_nA$ is the fully protonated acid, n is the number of protons in the fully protonated acid and $H_{n-1}A$ is the conjugate base of the acid corresponding to loss of one proton.

The acidity constant (Kn) for this equilibrium is therefore $$\frac{[H_nA]}{[H^+][H_{n-1}A]}$$

and $pK_a = \log_{10} K_n$

For the purposes of this specification, acidity constants are defined at 25° C. and at zero ionic strength. Literature values are taken where possible (see Stability Constants of Metal-Ion Complexes, Special Publication No. 25, The Chemical Society, London); where doubt arises they are determined by potentiometric titration using a glass electrode.

The $pK_a$ of the acidic anti-acne active used herein is preferably in the range of from about 1 to about 6, more preferably from about 1 to about 4.5, especially from about 1.5 to about 4.0.

The pH of the final aqueous/alcoholic anti-acne active solution is preferably in the range of from about 1 to about 7, more preferably from about 2 to about 5, especially from about 2 to about 4. At pH values of less than about 5 the aqueous phase is preferably free of acid labile species such as acrylic acid/ethyl acrylate copolymers and polyglycerylmethacrylate.

Another essential component of the compositions herein is a coalescence inhibitor for preventing coalescence of the aqueous phases. Preferably the coalescence inhibitor is an electrolyte or mixture of electrolytes, preferably sodium chloride. The coalescence inhibitor is present at a level of from about 0.05% to about 5%, preferably from about 0.01% to about 2% by weight of composition.

The compositions of the invention are in the form of a multiple phase water-in-oil emulsion comprising two or more aqueous phases As mentioned hereinabove the compositions of the invention comprise at least a first aqueous phase which comprises an anti-acne active in the form of an aqueous/alcoholic solution. This first aqueous phase preferably comprises no more than about 20% by weight of water. The compositions of the invention also comprise a second aqueous phase which preferably comprises at least about 15% by weight of composition of water. Preferably the compositions of the invention comprise in total from about 30% to about 50% by weight of water and about 1% to about 15% by weight of alcoholic solvent. The compositions herein will generally comprise anti-acne active in an amount exceeding its solubility in an equivalent mixture of water and solvent measured under ambient conditions (25° C.). It is a feature of the invention however that by virtue of the multiple phase form of the composition and the use of a coalescence inhibitor as described herein, the anti-acne material can be formulated in soluble form at levels exceeding its normal solubility in a single phase water/alcohol system.

Preferably the compositions of the invention comprise a pyrrolidone-based complexing agent. The pyrrolidone-based complexing agent is useful herein from the viewpoint of aiding solubilization of the anti-acne active and also an interfacial film former for the aqueous phases for preventing coalescence of the aqueous phases. The pyrrolidone-based complexing agent used herein is preferably selected from polyvinylpyrrolidone complexing agents or $C_1$–$C_4$ alkyl polyvinylpyrrolidone complexing agents having a molecular weight (viscosity average) in the range from about 1500 to about 1,500,000, preferably from about 3000 to about 700,000, more preferably from about 5000 to about 100,000. Suitable examples of pyrrolidone-based complexing agents are polyvinylpyrrolidone (PVP) (or povidone) and butylated polyvinylpyrrolidone. The most preferred pyrrolidone-based complexing agent herein is a polyvinylpyrrolidone complexing agent. PVP is commercially available under the trade name Luviskol (RTM) from BASF. A preferred PVP complexing agent herein is Luviskol K17 which has a viscosity-average molecular weight of about 9,000. Other pyrrolidone-based complexing agents for use herein include $C_1$–$C_{18}$ alkyl or hydroxyalkyl pyrrolidones such as lauryl pyrrolidone.

The pyrrolidone-based complexing agent is present in the composition herein in a level of from about 0.1% to about 10%, preferably from about 0.1% to about 5% by weight of composition. The weight ratio of anti-acne active:pyrrolidone-based complexing agent is in the range from about 10:1 to about 1:10, preferably from about 5:1 to about 1:5.

Preferred embodiments of the invention additionally comprise from about 0.01% to about 5%, preferably from about 0.1% to about 1%, especially from about 0.1% to about 0.5% by weight of an acid or salt thereof which is soluble in water at pH values of less than or equal to the $pK_a$ of the corresponding acid, for example, an acid selected from citric acid, boric acid, and salts, and mixtures thereof. These materials are valuable herein in combination with the pyrrolidone-based complexing agent from the viewpoint of aiding solubilization of the anti-acne active. Particularly preferred herein from this viewpoint is a sodium salt of citric acid. In preferred embodiments, the acid or salt thereof is soluble to a level of at least 5% w/w at 25° C.

The composition of the invention is in the form of a multiple phase water-in-oil emulsion containing two or more, preferably two discrete internal aqueous phases. In preferred embodiments the oil phase comprises a mixture of volatile silicones and non-volatile silicones. The silicone oil is present in an amount of from about 1% to about 50% by weight. Suitable volatile silicone oils include cyclic and linear volatile polyorganosiloxanes (as used herein, "volatile" refers to those materials which have a measurable vapour pressure at ambient conditions).

A description of various volatile silicones is found in Todd, et al. "Volatile Silicone Fluids for Cosmetics", 91 Cosmetics and Toiletries 27–32 (1976).

Preferred cyclic silicones include polydimethylsiloxanes containing from about 3 to about 9 silicon atoms, preferably containing from about 4 to about 5 silicon atoms. Preferred linear silicone oils include the polydimethylsiloxanes containing from about 3 to about 9 silicon atoms. The linear volatile silicones generally have viscosities of less than about 5 centistokes at 25° C., while the cyclic materials have viscosities of less than about 10 centistokes. Examples of silicone oils useful in the present invention include: Dow Corning 344, Dow Corning 21330, Dow Corning 345, and Dow Corning 200 (manufactured by the Dow Corning Corporation): Silicone 7207 and Silicone 7158 (manufactured by the Union Carbide Corporation). SF:202 (manufactured by General Electric) and SWS-03314 (manufactured by Stauffer Chemical).

Suitable non-volatile silicones preferably have an average viscosity of from about 1,000 to about 2,000,000 mm$^2$.s$^{-1}$ at 25° C. more preferably from about 10,000 to about 1,800,000 mm$^2$.s$^{-1}$, even more preferably from about 100,000 to about 1,500,000 mm$^2$.s$^{-1}$. Lower viscosity non-volatile silicone conditioning agents, however, can also be used. Viscosity can be measured by means of a glass capillary viscometer as set forth in Dow Corning Corporate Test Method CTM0004, Jul. 20, 1970. Suitable non-volatile silicone fluids for use herein include polyalkyl siloxanes, polyaryl siloxanes, polyalkylaryl siloxanes, polysiloxanes with amino functional substitutions, polyether siloxane copolymers, and mixtures thereof. The siloxanes useful in the present invention may be endcapped with any number of moieties, including, for example, methyl, hydroxyl, ethylene oxide, propylene oxide, amino and carboxyl. However, other silicone fluids having skin conditioning properties may be used. The non-volatile polyalkyl siloxane fluids that may be used include, for example, polydimethylsiloxanes. These siloxanes are available, for example, from the General Electric Company as a Viscasil (RTM) series and from Dow Corning as the Dow Corning 200 series. Preferably, the viscosity ranges' from about 10 mm$^2$.s$^{-1}$ to about 100,000 mm$^2$.s$^{-1}$ at 25° C. The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid. The polyether siloxane copolymer that may be used includes, for example, a polypropylene oxide modified dimethylpolysiloxane (e.g., Dow Corning DC-1248) although ethylene oxide or mixtures of ethylene oxide and propylene oxide may also be used.

References disclosing suitable silicone fluids include U.S. Pat. No. 2,826,551, Green; U.S. Pat. No. 3,964,500, Drakoff, issued Jun. 22, 1976; U.S. Pat. No. 4,364,837, Pader; and GB-A-849,433, Woolston. In addition, *Silicone Compounds* distributed by Petrach Systems Inc., 1984 provides an extensive (though not exclusive) listing of suitable silicone fluids.

Preferred non-volatile silicones for use herein include polydiorganosiloxane-polyoxyalkylene copolymers containing at least one polydiorganosiloxane segment and at least one polyoxyalkylene segment, said polydiorganosiloxane segment consisting essentially of

siloxane units wherein b has a value of from about 0 to about 3, inclusive, there being an average value of approximately 2 R radicals per silicon for all siloxane units in the copolymer, and R denotes a radical selected from methyl, ethyl, vinyl, phenyl and a divalent radical bonding said polyoxyalkylene segment to the polydiorganosiloxane segment, at least about 95% of all R radicals being methyl; and said polyoxyalkylene segment having an average molecular weight of at least about 1000 and consisting of from about 0 to about 50 mol percent polyoxypropylene units and from about 50 to about 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from about 2 to about 8. Such polymers are described in U.S. Pat. No. 4,268,499.

More preferred for use herein are polydiorganosiloxane-polyoxyalkylene copolymers having the general formula:

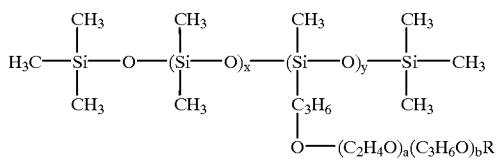

wherein x and y are selected such that the weight ratio of polydiorganosiloxane segments to polyoxalkylene segments is from about 2 to about 8, the mol ratio of a:(a+b) is from about 0.5 to about 1, and R is a chain terminating group, especially selected from hydrogen; hydroxyl; alkyl, such as methyl, ethyl, propyl, butyl, benzyl; aryl, such as phenyl; alkoxy such as methoxy, ethoxy, propoxy, butoxy; benzyloxy; aryloxy, such as phenoxy; alkenyloxy, such as vinyloxy and allyloxy; acyloxy, such as acetoxy, acryloxy and propionoxy and amino, such as dimethylamino.

The number of and average molecular weights of the segments in the copolymer are such that the weight ratio of polydiorganosiloxane segments to polyoxyalkylene segments in the copolymer is preferably from about 2.5 to about 4.0.

Suitable copolymers are available commercially under the tradenames Belsil (RTM) from Wacker-Chemie GmbH, Geschaftsbereich S, Postfach' D-8000 Munich 22 and Abil (RTM) from Th. Goldschmidt Ltd,. Tego House, Victoria Road, Ruislip, Middlesex, HA4 OYL. Particularly preferred for use herein are Belsil (RTM) 6031, Abil (RTM) B88183 and DC3225C. A preferred silicone herein is known by its CTFA designation as dimethicone copolyol.

The silicone oil phase preferably comprises from about 2% to about 25%, more preferably from about 5% to about 15% by weight of composition of non-volatile silicones.

A highly preferred component of the compositions herein is a humectant or mixture of humectants. The humectant or mixture of humectants herein is present in an amount of from about 0.1% to about 30% preferably from about 5% to about 25%, and more preferably from about 10% to about 20% by weight of composition. The humectant or mixture of humectants is preferably present in one or more of the aqueous phases.

The humectant can be incorporated at least partly into the oil phase of the water-in-oil emulsion so as to form a multiphase humectant-in-oil-in-water dispersion. The oil phase can comprise from about 0.1% to about 10%, more preferably from about 0.1% to about 3% by weight of humectant on a composition basis. The humectant can be introduced into the oil phase in the form of a mixture with or incorporated within a particulate lipophilic or hydrophobic carrier material.

Suitable humectants include sorbitol, panthenols, propylene glycol, butylene glycol, hexylene glycol, alkoxylated glucose derivatives, such as Glucam (RTM) E-20, hexanetriol, and glucose ethers, and mixtures thereof. Urea is also suitably added as a humectant in one or more of the internal aqueous phases.

The panthenol moisturiser can be selected from D-panthenol ([R]-2,4-dihydroxy-N-[3-hydroxypropyl)]-3,3-dimethylbutamide), DL-panthenol, calcium pantothenate, royal jelly, panthetine, pantotheine, panthenyl ethyl ether, pangamic acid, pyridoxin, pantoyl lactose and Vitamin B complex.

The preferred humectant herein is glycerine. Chemically, glycerine is 1,2,3-propanetriol and is a product of commerce.

Preferred embodiments herein comprise a pigment or mixture of pigments. Suitable pigments for use herein can be inorganic and/or organic. Also included within the term pigment are materials having a low colour or lustre such as matte finishing agents, and also light scattering agents. Examples of suitable pigments are iron oxides, acyl-glutamate iron oxides, ultramarine blue, D&C dyes, carmine, and mixtures thereof.

The composition of the invention can also include at least one matte finishing agent. The function of the matte finishing agent is to hide skin defects and reduce shine. Such cosmetically acceptable inorganic agents, i.e., those included in the CTFA Cosmetic Ingredient Dictionary, Third Ed., as silica, hydrated silica, silicone-treated silica beads, mica, talc, polyethylene, titanium dioxide, bentonite, hectorite, kaolin, chalk, diatomaceous earth, zinc oxide (USP or ultrafine) and the like may be utilized. Of particular usefulness as a matte finishing agent is low lustre pigment such as titanated mica (mica coated with titanium dioxide) coated with barium sulfate. Of the inorganic components useful as a matte finishing agent low lustre pigment, talc, polyethylene, hydrated silica, kaolin, titanium dioxide and mixtures thereof are particularly preferred.

Materials suitable for use herein as light-scattering agents can be generally described as spherical shaped inorganic materials having a particle size of up to about 100 microns, preferably from about 5 to about 50 microns, for example spherical silica particles.

The total concentration of the pigment may be from about 0.1 to about 25% by weight and is preferably from about 1 to about 10% by weight of the total composition, the exact concentration being dependent to some extent upon the specific mixture of pigments selected to achieve the desired shades. The preferred compositions contain from about 2% to about 20% by weight of titanium dioxide and most preferably from about 5% to about 10% by weight of titanium dioxide.

The preferred pigments for use herein from the viewpoint of moisturisation, skin feel, skin appearance and emulsion compatibility are treated pigments. The pigments can be treated with compounds such as amino acids such as lysine, silicones, lauroyl, collagen, polyethylene, lecithin and ester oils. The more preferred pigments are the silicone (polysiloxane) treated pigments.

In preferred embodiments of the invention the water is present in two discrete internal aqueous phases, the anti-acne active only being present in one of the aqueous phases. This is particularly beneficial from the viewpoint of being able to provide a stable composition having a high water level without precipitation of the anti-acne active out of solution.

The compositions of the present invention can also comprise a particulate cross-linked hydrophobic acrylate or methacrylate copolymer. This copolymer is particularly valuable for reducing shine and controlling oil while helping to provide effective moisturization benefits. The cross-linked hydrophobic polymer is preferably in the form of a copolymer lattice with at least one active ingredient dispersed uniformly throughout and entrapped within the copolymer lattice. Alternatively, the hydrophobic polymer can take the form of a porous particle having a surface area ($N_2$-BET) in the range from about 50 to 500, preferably 100 to 300 $m^2/g$ and having the active ingredient absorbed therein.

The cross-linked hydrophobic polymer when used herein is in an amount of from about 0.1% to about 10% by weight and is preferably incorporated in the external silicone-containing oil phase. The active ingredient can be one or more or a mixture of skin compatible oils, skin compatible humectants, emollients, moisturizing agents and sunscreens. The polymer material is in the form of a powder, the powder being a combined system of particles. The system of powder particles forms a lattice which includes unit particles of less than about one micron in average diameter, agglomerates of fused unit particles of sized in the range of about 20 to 100 microns in average diameter and aggregates of clusters of fused agglomerates of sizes in the range of about 200 to 1,200 microns in average diameter.

The powder material of the present invention which can be employed as the carrier for the active ingredient can be broadly described as a cross-linked "post absorbed" hydrophobic polymer lattice. The powder preferably has entrapped and dispersed therein, an active which may be in the form of a solid, liquid or gas. The lattice is in particulate form and constitutes free flowing discrete solid particles when loaded with the active material. The lattice may contain a predetermined quantity of the active material. The polymer has the structural formula:

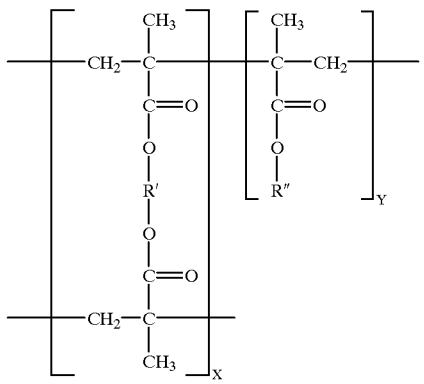

where the ratio of x to y is 80:20, R' is —$CH_2CH_2$— and R" is —$(CH_2)_{11}CH_3$.

The hydrophobic polymer is a highly crosslinked polymer, more particularly a highly cross-linked polymethacrylate copolymer. The material is manufactured by the Dow Corning Corporation, Midland. Mich., USA, and sold under the trademark POLYTRAP (RTM). It is an ultralight free-flowing white powder and the particles are capable of absorbing high levels of lipophilic liquids and some hydrophilic liquids while at the same time maintaining a free-flowing powder character. The powder structure consists of a lattice of unit particles less than one micron that are fused into agglomerates of 20 to 100 microns and the agglomerates are loosely clustered into macro-particles or aggregates of about 200 to about 1200 micron size. The polymer powder is capable of containing as much as four times its weight of fluids, emulsions, dispersions or melted solids.

Adsorption of actives onto the polymer powder can be accomplished using a stainless steel mixing bowl and a spoon, wherein the active is added to the powder and the spoon is used to gently fold the active into the polymer powder. Low viscosity fluids may be adsorbed by addition of the fluids to a sealable vessel containing the polymer and then tumbling the materials until a consistency is achieved. More elaborate blending equipment such as ribbon or twin cone blenders can also be employed. The preferred active ingredient for use herein is glycerine. Preferably, the weight ratio of humectant:carrier is from about 1:4 to about 3:1.

Also suitable as a highly cross-linked polymethacrylate copolymer is Microsponges 5647. This takes the form of generally spherical particles of cross-linked hydrophobic polymer having a pore size of from about 0.01 to about 0.05μm and a surface area of 200–300 m$^2$/g. Again, it is preferably loaded with humectant in the levels described above.

The compositions of the invention can also contain a hydrophilic gelling agent at a level preferably from about 0.01% to about 10%, more preferably from about 0.02% to about 2%, and especially from about 0.02% to about 0.5%. The gelling agent preferably has a viscosity (1% aqueous solution, 20° C., Brookfield RVT) of at least about 4000 mPa.s, more preferably at least about 10,000 mPa.s and especially at least 50,000 mPa.s.

Suitable hydrophilic gelling agents can generally be described as water-soluble or colloidally water-soluble polymers, and include cellulose ethers (e.g. hydroxyethyl cellulose, methyl cellulose, hydroxypropylmethyl cellulose), polyvinylalcohol, polyquaternium-10, guar gum, hydroxypropyl guar gum and xanthan gum.

Other suitable gelling agents suitable for use herein are oleogels such as trihydroxystearin and aluminium magnesium hydroxy stearate. The gelling agents herein are particularly valuable for providing excellent stability characteristics over both normal and elevated temperatures.

The compositions herein can additionally comprise an emollient. Emollients suitable for the compositions of the present invention include natural and synthetic oils selected from mineral, vegetable, and animal oils, fats and waxes, fatty acid esters, fatty alcohols, alkylene glycol and polyalkylene glycol ethers and esters, fatty acids and mixtures thereof.

Suitable emollients for use herein include, for example, optionally hydroxy-substituted $C_8$–$C_{50}$ unsaturated fatty acids and esters thereof, $C_1$–$C_{24}$ esters of $C_8$–$C_{30}$ saturated fatty acids such as isopropyl myristate, cetyl palmitate and octyldodecylmyristate (Wickenol 142), beeswax, saturated and unsaturated fatty alcohols such as behenyl alcohol and cetyl alcohol, hydrocarbons such as mineral oils, petrolatum and squalane, fatty sorbitan esters (see U.S. Pat. No. 3,988,255, Seiden, issued Oct. 26, 1976), lanolin and lanolin derivatives, such as lanolin alcohol ethoxylated, hydroxylated and acetylated lanolins, cholesterol and derivatives thereof, animal and vegetable triglycerides such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil and $C_1$–$C_{24}$ esters of dimer and trimer acids such as diisopropyl dimerate, diisostearylmalate, diisostearyldimerate and triisostearyltrimerate.

Preferred emollients are selected from hydrocarbons such as isohexadecane, mineral oils, petrolatum and squalane, lanolin alcohol, and stearyl alcohol. These emollients may be used independently or in mixtures and may be present in the composition of the present invention in an amount from about 1% to about 30% by weight, and preferably are present in an amount from about 5% to about 15% by weight of the total composition.

The composition may also contain additional materials such as, for example, fragrances, fillers such as nylon, sun-screens, preservatives, proteins, antioxidants, chelating agents and water-in-oil emulsifiers as appropriate.

Another optional component of the make-up composition is one or more ultraviolet absorbing agents. Ultraviolet absorbing agents, often described as sunscreening agents, can be present in a concentration in the range of between about 1% and about 12% by weight, based on the total weight of composition. Preferably, the UV absorbing agents constitute between about 2% and 8% by weight. More preferably, the UV absorbing agents can be present in the composition in a concentration range of between about 4% and about 6% by weight. Of the ultraviolet absorbing agents suitable for use herein, benzophenone-3, octyl dimethyl PABA (Padimate 0) and mixtures thereof are particularly preferred.

Another optional but preferred component herein is one or more additional chelating agents, preferably in the range of from about 0.02% to about 0.10% by weight, based on the total weight of the composition. Preferably, the chelating agent is present in a concentration in the range of between about 0.03% and about 0.07% by weight, based on the total weight of the composition. Among the chelating agents that may be included in the composition is tetrasodium EDTA.

Another optional but preferred component of the cosmetic composition is one or more preservatives. The preservative concentration in the foundation composition, based on the total weight of that composition, is in the range of between about 0.05% and about 0.8% by weight, preferably between about 0.1% and about 0.3% by weight. Suitable preservatives for use herein include sodium benzoate and propyl paraben, and mixtures thereof.

The cosmetic compositions of the present invention can be in the form of moisturising creams, lotions or gels, and pigmented compositions such as tinted moisturisers, foundation and liquid concealers.

The following Table is provided to illustrate compositions of the present invention:

| Example | I Wt % | II Wt % | III Wt % | IV Wt % | V Wt % | VI Wt % | VII Wt % |
|---|---|---|---|---|---|---|---|
| A. | | | | | | | |
| Cetyloctanoate | 1.00 | 0.0 | 0.0 | 0.0 | 0.0 | 0.0 | 2.0 |
| Cyclomethicone | 8.57 | 8.0 | 8.3 | 9.0 | 12.0 | 8.57 | 8.57 |
| Cyclomethicone/ dimethicone copolyol (90:10) | 12.00 | 12.5 | 11.5 | 12.1 | 12.3 | 11.00 | 12.1 |
| Propylparaben (33%) in laureth-7 | 0.75 | 0.75 | 0.0 | 0.75 | 0.0 | 0.75 | 0.75 |
| Dimethicone Fluid | 0.0 | 0.0 | 2.0 | 0.0 | 0.0 | 0.0 | 0.0 |
| Benzophenene-3 | 0.0 | 0.0 | 0.0 | 0.0 | 0.0 | 2.0 | 0.0 |
| Propylene glycol Dicaprylate/ Dicaprate | 0.0 | 0.0 | 0.0 | 4.0 | 0.0 | 5.0 | 0.0 |
| Isopropyl Palmitate | 3.0 | 0.0 | 3.0 | 0.0 | 4.0 | 0.0 | 0.0 |
| B. | | | | | | | |
| Titanium Dioxide (silicone treated) | 2.0 | 2.0 | 2.5 | 2.0 | 3.0 | 3.5 | 2.6 |
| Titanium Dioxide treated (Aluminium | 2.0 | 2.0 | 1.0 | 1.5 | 1.8 | 2.1 | 1.0 |

-continued

| Example | I Wt % | II Wt % | III Wt % | IV Wt % | V Wt % | VI Wt % | VII Wt % |
|---|---|---|---|---|---|---|---|
| hydrate, stearic acid) | | | | | | | |
| Titanated Micas | 0.1 | 0.0 | 0.0 | 0.0 | 0.0 | 0.0 | 0.1 |
| Talc | 3.38 | 4.5 | 5.0 | 0.7 | 0.7 | 0.7 | 3.38 |
| Silica | 0.6 | 0.0 | 0.0 | 0.0 | 0.6 | 0.0 | 0.0 |
| Nylon | 0.0 | 0.0 | 0.0 | 0.0 | 0.5 | 0.0 | 0.0 |
| Zinc Oxide (Microfine) | 2.0 | 2.0 | 1.0 | 2.0 | 2.0 | 2.0 | 2.0 |
| C. | | | | | | | |
| Cyclomethicone/ | 0.5 | 0.5 | 0.5 | 0.5 | 0.5 | 0.5 | 0.5 |
| D. | | | | | | | |
| Yellow Iron Oxide | 0.5 | 0.6 | 0.52 | 0.53 | 0.61 | 0.54 | 0.5 |
| Red Iron Oxide | 0.28 | 0.3 | 0.31 | 0.25 | 0.27 | 0.2 | 0.3 |
| Black Iron Oxide | 0.05 | 0.1 | 0.07 | 0.05 | 0.06 | 0.07 | 0.1 |
| E. | | | | | | | |
| Synthetic Wax | 0.1 | 0.5 | 0.5 | 0.1 | 0.0 | 0.0 | 0.0 |
| Arachidyl behenate | 0.3 | 0.0 | 0.0 | 0.3 | 0.5 | 0.3 | 0.3 |
| Stearic Acid | 0.0 | 0.0 | 0.0 | 0.0 | 0.0 | 0.0 | 2.5 |
| Palmitic Acid | 0.0 | 0.0 | 0.0 | 0.0 | 0.0 | 2.5 | 0.0 |
| Silica (Spheron P1500) | 0.1 | 0.0 | 0.1 | 0.0 | 0.1 | 0.0 | 0.1 |
| F. | | | | | | | |
| Trihydroxy-stearin | 0.3 | 0.3 | 0.5 | 0.6 | 0.0 | 0.0 | 0.0 |
| Cyclomethicone | 1.0 | 1.0 | 0.0 | 0.0 | 1.0 | 1.0 | 1.0 |
| Beeswax | 1.5 | 1.2 | 0.0 | 0.0 | 1.3 | 0.0 | 0.0 |
| Abil WED9 | 0.0 | 3.0 | 0.0 | 0.0 | 0.0 | 0.0 | 0.0 |
| G. | | | | | | | |
| Ethylene brassylate | 0.05 | 0.0 | 0.0 | 0.0 | 0.0 | 0.05 | 0.05 |
| BHT | 0.05 | 0.0 | 0.0 | 0.0 | 0.0 | 0.05 | 0.05 |
| H. | | | | | | | |
| Deionized water | 7.55 | 7.6 | 7.7 | 7.65 | 7.6 | 7.4 | 7.63 |
| Ethanol | 4.0 | 5.5 | 4.0 | 8.0 | 4.5 | 5.0 | 4.0 |
| Salicylic acid | 1 | 1 | 1 | 2 | 2 | 2 | 0.0 |
| Azeleic acid | 0.0 | 0.0 | 0.0 | 0.0 | 0.0 | 0.0 | 5 |
| Dipropylene glycol | 6.0 | 5.0 | 6.5 | 7.00 | 8.0 | 6.0 | 5.0 |
| Polyvinylpyrroli-done (Luviskol K17) | 1 | 2 | 1.5 | 1 | 1 | 1 | 2 |
| Sodium citrate | 0.3 | 0.3 | 0.3 | 0.2 | 0.4 | 0.3 | 0.4 |
| I. | | | | | | | |
| Deionized water | 12.0 | 12.2 | 11.5 | 11.8 | 12.0 | 12.1 | 12.2 |
| Sodium chloride | 0.2 | 0.2 | 0.2 | 0.2 | 0.1 | 0.2 | 0.1 |
| Tetrasodium EDTA | 0.04 | 0.04 | 0.04 | 0.04 | 0.04 | 0.04 | 0.04 |
| Glycerin | 4 | 4 | 4 | 4 | 4 | 4 | 4 |
| J. | | | | | | | |
| Deionized water | | | | to 100 | | | |
| Sodium chloride | 0.2 | 0.3 | 0.2 | 0.3 | 0.3 | 0.3 | 0.4 |
| Polyvinylpyrrolid-one (Luviskol K17) | 0.5 | 0.0 | 0.0 | 0.6 | 1.0 | 0.8 | 0.0 |
| Tetrasodium EDTA | 0.06 | 0.06 | 0.06 | 0.06 | 0.06 | 0.06 | 0.06 |
| Glycerin | 6.0 | 6.0 | 6.0 | 6.0 | 6.0 | 6.0 | 6.0 |
| Sodium Citrate | 0.1 | 0.0 | 0.1 | 0.2 | 0.0 | 0.0 | 0.0 |
| K. | | | | | | | |
| Deionized Water | 0.0 | 0.0 | 0.0 | 0.0 | 10.0 | 0.0 | 0.0 |
| L. | | | | | | | |
| Propylene Glycol | 0.0 | 0.0 | 0.0 | 2.0 | 0.0 | 0.0 | 0.0 |
| Xanthan Gum | 0.0 | 0.0 | 0.0 | 0.08 | 0.0 | 0.0 | 0.0 |
| M. | | | | | | | |
| Essential Oils | 0.0 | 0.0 | 0.0 | 0.20 | 0.0 | 0.0 | 0.0 |
| Perfume Oil | 0.0 | 0.25 | 0.0 | 0.20 | 0.0 | 0.0 | 0.0 |
| Vitamin A Palmitate | 0.0 | 0.05 | 0.0 | 0.0 | 0.0 | 0.0 | 0.0 |
| N. | | | | | | | |
| Aloe Vera Gel | 0.0 | 0.0 | 3.0 | 0.0 | 0.0 | 0.0 | 0.0 |
| Chamomile Extract | 0.0 | 0.0 | 0.1 | 0.0 | 0.0 | 0.0 | 0.0 |

*Contains about 1% propylene glycol.

The various components listed in the Table have been segregated into groups, the constituents of each group being mixed together before being added to members of the remaining groups in accordance with the procedures set forth below.

In the first step, the mixture of components of phase A is stirred for approximately 5 minutes with sheer mixing until homogeneous. With high speed sheer mixing, the materials of phase B are added gradually to A and the batch is mixed for 20 minutes until dispersed.

The components of phase C and then phase D are slowly added to the mixture of phases A and B with high shear mixing until dispersed. Silica is added at this point and dispersed through the mixture.

The resulting batch heated to 90° C. before the addition of the components of phase E. The vessel is cooled to 55° C. and the premixed phase F is added. The batch is mixed until homogeneous. The mixture is cooled to 30° C. and phase G is added.

Phase H is prepared by first dissolving the polyvinylpyrrolidone complexing agent in alcoholic solvent and then dissolving the anti-acne active followed by the remaining components, ending with adding a solution of citric acid or salt. Phase I is then added to phase H and the resulting mixture is added to the oil phase. Premixed phase J is then also added to the oil phase.

Finally phases K, L, M and N are added as diluent.

The resulting composition is ready for packaging.

The compositions of the Examples exhibit moisturisation, anti-acne activity, skin anti-ageing benefits, together with improved formulation and colour stability, skin feel and appearance.

We claim:

1. An anti-acne cosmetic composition in the form of a multiple phase water-in-oil emulsion, wherein the composition comprises:
   (a) two or more aqueous phases; and
   (b) a coalescence inhibitor for preventing coalescence of the aqueous phases;

and wherein at least a first aqueous phase comprises an anti-acne active in the form of an aqueous/alcoholic solution.

2. An anti-acne cosmetic composition according to claim 1 wherein the coalescence inhibitor is an electrolyte or mixture of electrolytes.

3. An anti-acne cosmetic composition according to claim 2 wherein the electrolyte is sodium chloride.

4. An anti-acne cosmetic composition according to claim 1 wherein the coalescence inhibitor is present at a level of from about 0.05% to about 5% by weight of composition.

5. An anti-acne cosmetic composition according to claim 1 wherein the coalescence inhibitor is present at a level of from 0.01% to about 1% by weight of composition.

6. An anti-acne cosmetic composition according to claim 1 wherein the first aqueous phase comprises no more than 20% by weight of composition of water.

7. An anti-acne cosmetic composition according to any of claim 1 comprising a second aqueous phase which comprises at least about 15% by weight of composition of water.

8. An anti-acne cosmetic composition according to claim 1 comprising in total from about 30% to about 50% by weight of water and from about 1% to about 15% by weight of alcoholic solvent, and wherein the composition comprises anti-acne active in an amount exceeding its solubility in an equivalent mixture of water and solvent.

9. An anti-acne cosmetic composition according to claim 1 wherein the anti-acne active is selected from salicylic acid, retinoic acid, azelaic acid, lactic acid, glycolic acid, pyruvic acid, flavonoids, and derivatives and mixtures thereof.

10. An anti-acne cosmetic composition according to claims 9 comprising from about 0.1% to about 10% by weight of the anti-acne active.

11. An anti-acne cosmetic composition according to any of claims 1 comprising from about 1% to about 50% by weight of silicone oil selected from volatile silicones, non-volatile silicones and mixtures thereof.

12. An anti-acne cosmetic composition according to claim 11 wherein the volatile silicone oil is selected from cyclic polyorganicsiloxanes having viscosities less than about 10 centistokes and linear polyorganosiloxanes having viscosities of less than about 5 centistokes at 25° C., and mixtures thereof.

13. An anti-acne cosmetic composition according to claim 12 wherein the volatile silicone oil is selected from cyclic polydimethylsiloxanes containing from about 3 to about 9 silicon atoms and linear polydimethylsiloxanes containing from about 3 to about 9 silicon atoms.

14. An anti-acne cosmetic compositions according to claim 13 wherein the non-volatile silicone oil comprises a polydiorganosiloxane-polyoxyalkylene copolymer containing at least one polydiorganosiloxane segment and at least one polyoxyalkylene segment.

15. An anti-acne cosmetic composition according to claim 14 wherein the polydiorganosiloxane-polyoxyalkylene copolymer is dimethicone copolyol.

16. An anti-acne cosmetic composition according to claim 1 additionally comprising from about 0.1% to about 30% by weight of humectant.

17. An anti-acne cosmetic composition according to claim 16 wherein the humectant is glycerin.

18. An anti-acne cosmetic composition according to claim 1 comprising from about 0.01% to about 10% by weight of pigment or mixture of pigments.

19. An anti-acne cosmetic composition according to claim 10 wherein the anti-acne active is salicylic acid.

20. An anti-acne cosmetic composition according to claim 1 additionally comprising from about 0.1% to about 10% by weight of polyvinylpyrrolidone complexing agent.

21. An anti-acne cosmetic composition according to claim 1 additionally comprising from about 0.01% to about 5% by weight of citric acid or salt thereof.

22. An anti-acne cosmetic composition according to claim 21 wherein the silicone oil comprises from about 2% to about 25% by weight of compositions of non-volatile silicones.

23. An anti-acne cosmetic composition according to claim 1 additonally comprising from about 1% to about 15% by weight of an emollient which is a natural or synthetic oil selected from mineral, vegetable and animal oils, fats and waxes, fatty acid esters, fatty alcohols, alkylene glycol and polyalkylene glycol ethers and esters, fatty acids and mixtures thereof.

24. An anti-acne cosmetic composition according to claim 23 wherein the emollient is selected from isopropylpalmitate, isopropyl isostearate, dioctyl maleate, propylene glycol dicaprylate/propylene glycol dicaprate, caprylic triglyceride/capric triglyceride, squalane, mineral oil, cetearylisononanoate and lanolin alcohol, and mixtures thereof.

25. An anti-acne cosmetic composition according to claim 1 wherein the aqueous/alcoholic solution of anti-acne active has a pH of from about 1 to about 7.

26. Process for preparing an anti-acne composition according to claim 1, the process comprising the steps of:

(a) preparing the first aqueous phase by dissolving the anti-acne active in an aqueous/alcoholic solution;

(b) admixing the first aqueous phase with the oil phase; and (c) subsequently adding one or more additional aqueous phase or phases to the resulting mixture to form the multiple phase water-in-oil emulsion, the first and/or additional aqueous phase or phases having dissolved therein the coalescence inhibitor.

27. An anti-acne cosmetic composition according to claim 13 wherein the volatile silicone oil is selected from cyclic polydimethylsiloxanes containing from about 4 to about 5 silicon atoms and linear polydimethylsiloxanes containing from about 3 to about 9 silicon atoms.

28. An anti-acne cosmetic composition according to claim 22 wherein the silicone oil comprises from about 5% to about 15% by weight of compositions of non-volatile silicones.

29. An anti-acne cosmetic composition according to claim 25 wherein the aqueous/alcoholic solution of anti-acne active has a pH of from about 2 to about 5.

30. An anti-acne cosmetic composition according to claim 29 wherein the aqueous/alcoholic solution of anti-acne active has a pH of from about 2 to about 4.

* * * * *